(12) United States Patent
Simpson

(10) Patent No.: US 11,452,475 B2
(45) Date of Patent: Sep. 27, 2022

(54) SYSTEMS AND METHODS FOR ASSESSING AND IMPROVING SUSTAINED ATTENTION

(71) Applicant: Think-Now Inc., San Francisco, CA (US)

(72) Inventor: Gregory V. Simpson, San Anselmo, CA (US)

(73) Assignee: Think-Now Inc., San Francisco, CA (US)

( * ) Notice: Subject to any disclaimer, the term of this patent is extended or adjusted under 35 U.S.C. 154(b) by 551 days.

(21) Appl. No.: 16/428,955

(22) Filed: May 31, 2019

(65) Prior Publication Data

US 2019/0350510 A1 Nov. 21, 2019

Related U.S. Application Data

(60) Division of application No. 15/090,586, filed on Apr. 4, 2016, now Pat. No. 10,342,472, which is a continuation-in-part of application No. 13/933,024, filed on Jul. 1, 2013, now Pat. No. 9,378,658.

(60) Provisional application No. 62/143,704, filed on Apr. 6, 2015.

(51) Int. Cl.
| | |
|---|---|
| *A61B 5/38* | (2021.01) |
| *A61B 5/16* | (2006.01) |
| *G09B 7/02* | (2006.01) |
| *A61B 5/00* | (2006.01) |
| *G09B 19/00* | (2006.01) |
| *A61B 5/378* | (2021.01) |

(52) U.S. Cl.
CPC .............. *A61B 5/168* (2013.01); *A61B 5/378* (2021.01); *A61B 5/38* (2021.01); *A61B 5/6803* (2013.01); *A61B 5/6814* (2013.01); *G09B 7/02* (2013.01); *G09B 19/00* (2013.01)

(58) Field of Classification Search
CPC .......... A61B 5/16; A61B 5/00; A61B 5/0484; A61B 5/168; A61B 5/38; A61B 5/378; A61B 5/6803; A61B 5/6814; G09B 19/00; G09B 7/02
See application file for complete search history.

(56) References Cited

U.S. PATENT DOCUMENTS 6,402,520 B1 6/2002 Freer

OTHER PUBLICATIONS

Kim et al., "Classification of selective attention to auditory stimuli: Toward vision-free brain-computer interfacing," Journal of Neuroscience Methods 197 (2011) 180-185 (Year: 2011).*
Thomas Z. Lauritzen, Justin M. Ales, Alex R. Wade; The effects of visuospatial attention measured across visual cortex using source-imaged, steady-state EEG. Journal of Vision 2010;10(14):39 (Year: 2010).

(Continued)

*Primary Examiner* — Eric J Messersmith
(74) *Attorney, Agent, or Firm* — Kang S. Lim

(57) ABSTRACT

The present invention relates to a system and method for assessing and training the quality of attentional awareness and control of an individual. The individual's attention is monitored using a neurophysiological system such as EEG while using a computer system and display that provides signals that allow the correlation of behavioral measures of attention with neurophysiological measures. The combination of those signals is a novel, accurate and reliable system for assessing any individual's true attention capabilities.

12 Claims, 9 Drawing Sheets

(56) References Cited

OTHER PUBLICATIONS

Mairena, M.A., Martino, A.D., Dominguez-Martin, C. et ai.;Low frequency oscillations of response time explain parent ratings of inattention; Eur Child Adolesc Psychiatry (2012) 21: 101. (Year: 2012).

Adamo, N., Huo, L., Adelsberg, S. et al.; Response time intra-subject variability: commonalities between children with autism spectrum disorders and children with ADHD; Eur Child Adolesc Psychiatry (2014) 23: 69 (Year: 2014).

Bharadwaj HM, Lee AKC and Shinn-Cunningham BG (2014) Measuring auditory selective attention using frequency tagging. Front. Integr. Neurosci. 8:6 (Year: 2014).

Martino, et al.; "Decomposing Intra-Subject Variability in Children with Attention-Deficit/Hyperactivity Disorder," Biol Psychiatry 2008;64:607-614 (Year: 2008).

Adamo, et al., "Increased Response-Time Variability Across Different Cognitive Tasks in Children With ADHD," Journal of Attention Disorders, vol. 18, Issue 5, pp. 434-446 (Year: 2012).

\* cited by examiner

SYSTEMS AND METHODS FOR ASSESSING AND IMPROVING SUSTAINED ATTENTION

CROSS REFERENCE TO RELATED APPLICATIONS

This application is a divisional of U.S. patent application Ser. No. 15/090,586, filed Apr. 4, 2016, recently allowed, which is a non-provisional and claims the benefit of U.S. Provisional Application No. 62/143,704 filed Apr. 6, 2015, of the same title. Also, U.S. patent application Ser. No. 15/090,586 is a continuation-in-part of U.S. application Ser. No. 13/933,024 filed Jul. 1, 2013, entitled "Systems and Methods for Training Meta-Attention", now U.S. Pat. No. 9,378,658, which is hereby fully incorporated by reference, which applications are incorporated herein in their entirety by this reference.

BACKGROUND

The present invention relates to systems and methods for monitoring and training sustained attention of users.

Sustained attention is important because it is the foundation for being focused, effective and productive in nearly every cognitive process we use in everyday life (effective, productive); it is also a significant component of many cognitive clinical disorders (e.g. ADHD, autism, schizophrenia, depression, SAD, PTSD, TBI).

Continuous Performance Tests (CPTs) have proven useful as assessment tools in normal populations and for assessing the clinical disorders mentioned above. A major limitation has been in their ability to assess the suppression of distractors. Using behavioral tests, in which distractors are by definition irrelevant and not to be responded to, one can assess a person's ability to ignore distractors only indirectly—by detecting the rare instance when a person responds incorrectly to a distractor which is indicative of less attention to the target and/or less suppression of the distractor (although which is the cause is ambiguous). Consequently, the data includes a small quantity of rare errors. Poor distractor suppression can also be indirectly inferred by measuring differences in performance to a target as a function of the presence of distractors (e.g., when a target is preceded by a distractor versus when it is not preceded by a distractor). Therefore, CPT tests do not provide a direct measure of continuous suppression of distractors. The only way to obtain such a measure is with brain physiology measures.

In well-accepted models of attention and behavioral studies, it has been recognized that enhanced processing of targets and suppression of distractors are not simply opposite sides of the same attention coin. It has always been difficult to characterize the processing of distractors behaviorally because it must be accomplished indirectly (e.g., distractor disruption of performance to target; occasional errors, false alarms to non-targets; etc.). Using neurophysiological measures we can directly measure the processing of all distractors as well as target processing. We now know that attending and suppressing distractors are at least partially separable functions that are controlled in part by different brain regions. EEG and fMRI literature shows that deficits in attending vs. distractor suppression can be differentiated behaviorally and physiologically. Consequently, it makes sense that these processes can be differentiated within an individual and that they can contribute differentially to cognitive disorders. The important implication for the prescription of therapeutics is that therapeutics can be tailored to attention processes or distractor suppression processes, or both.

Two people can perform comparably with different configurations of brain processes. For example, one person may enhance target processing with little suppression of distractors, while the other person has little enhancement of target processing and strong suppression of competing distractor inputs. In both cases the target processing wins over the distractor processing and the result is a similar output measure (e.g., RT). However, the same training or therapeutic that addresses, for example, target processing would likely result in quite different changes in these people. Ideally, training would focus on attending for one person and ignoring (distractor suppression) for the other. We propose an assessment tool that characterizes both attending and ignoring will open the door to the development of new cognitive training and therapeutics that can emphasize these two related yet separable aspects of sustained attention.

Being able to continuously monitor performance and brain components of attending and ignoring opens the door for training/therapeutics that provides ongoing feedback during sustained attention tasks. This is essential to creating improved awareness of attention (meta-attention) and attentional control.

Consequently, it is apparent that an urgent need exists for the ability to determine an individual's "brain style", often referred to as "executive function", so that therapeutics can be applied that target one or the other aspect of attending/ignoring processes.

SUMMARY

To achieve the foregoing and in accordance with the present invention, a system and method for continuous monitoring and assessment of attention and improvement of attentional awareness and control is provided. In particular the system and methods for monitoring and assessment include an EEG system that allows for the continuous monitoring of brain activity. That EEG system has enough leads to reliably detect a steady state visually evoked potential (SSVEP) that is induced by a flickering image. That flickering image is presented to the individual through a computer screen and the flicker rate can vary widely, from 5 to 60 hertz.

As the individual is visually engaged with the screen, the flicker rate creates a signal of equivalent frequency that can be detected directly. In this embodiment, the screen presents two objects flickering at different rates. Both objects are in the visual field simultaneously. The individual is instructed to attend to one of the objects and ignore the other object.

Over the time frame of the assessment, a series of targets and distractors are presented to the individual in conjunction with the objects being attended or ignored. The individual is instructed to physically respond to only the targets presented in conjunction with attended object. All other distractors and targets are to be ignored and the individual is instructed to not physically respond.

During the assessment, the user is given a visual "fixation point" that the user is visually focused on so that to ignore and attend objects are in a clear visual field.

A computer monitors continuously the individual's behavioral responses and also their EEG signals. The assessment algorithm uses both data sets to make reliable and accurate measurements of the individual's ability to attend and ignore.

Repeated use of the method can constitute training of attentional awareness (meta-attention) and feedback about attending and ignoring brain activity levels can be used to train the user's attentional awareness and control.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which.

DETAILED DESCRIPTION

Figure 1A:
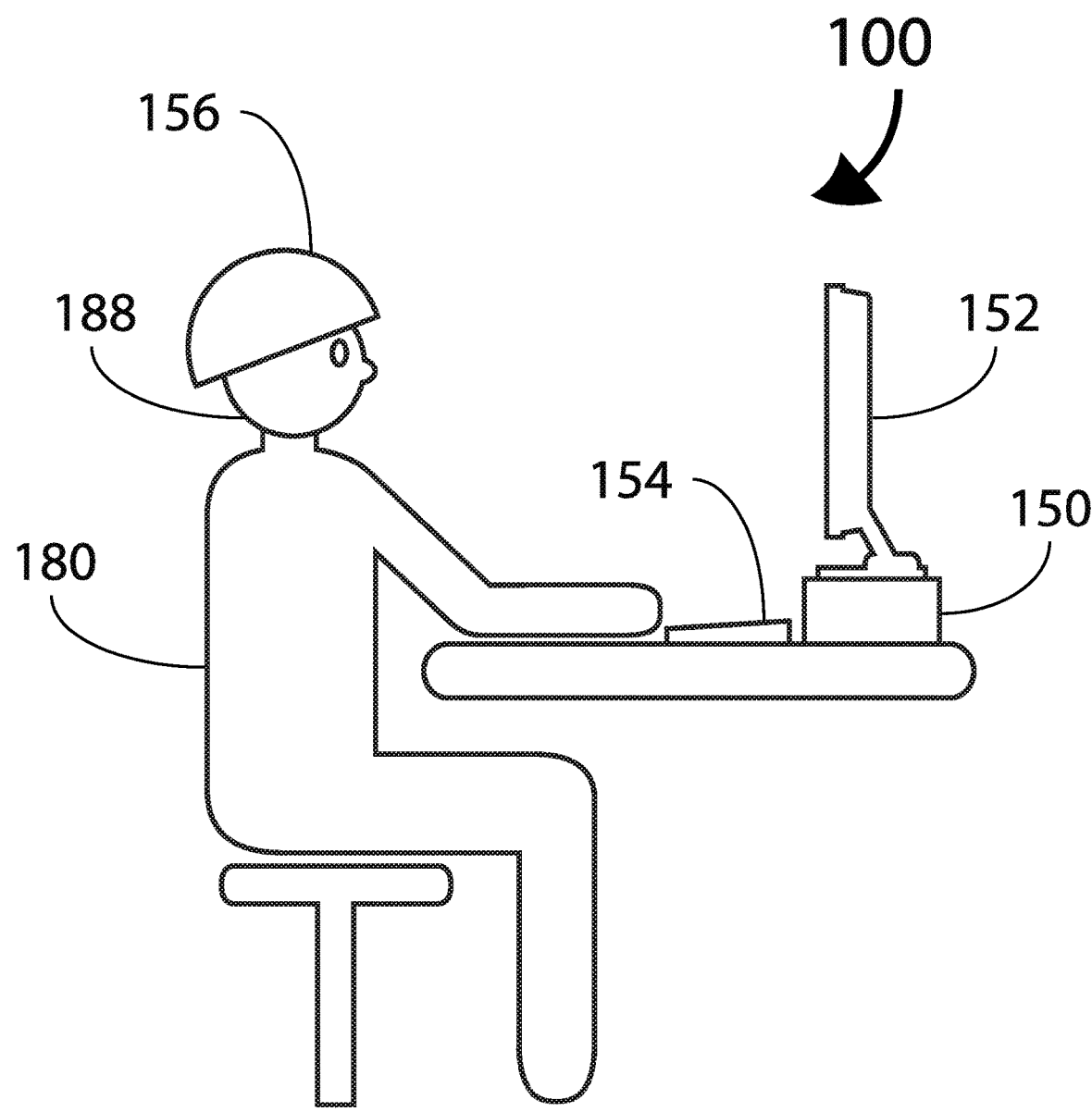
FIG. 1A illustrates one embodiment of an attention measuring system in accordance with the present invention.

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

The present invention relates to a system and methods for an objective, reliable and accurate assessment of an individual's attention. For example, Attention-Deficit/Hyperactivity Disorder (ADHD) is highly prevalent, and the methods for characterization of the disorder are limited, particularly with respect to neurophysiological biomarkers that can be made readily and inexpensively accessible to a wide market. We have created a novel neurophysiological attention test (NAT) based on electroencephalography (EEG) and we have successfully demonstrated the NAT's validity and utility as an assessment tool for ADHD providing two new biomarkers for ADHD The NAT provides critical new measures of the fluctuations in attentional control in ADHD in addition to standard performance measures. The neurophysiological measures of the NAT provide a closer link to brain research and brain-based models of ADHD and provide direct brain measures of treatment effects.

Attention-related deficits in ADHD are associated more with sustained attention than with selective. Deficits in selective attention, i.e. the top-down controlled processing of a target or distractor, are less prevalent under circumstances in which patients with ADHD properly allocate attentional control (e.g., high load). ADHD individual deficits lie in the ability to be consistently and purposefully in control of these top-down controlled selective attention processes. That is, an important aspect of ADHD would appear to be difficulty in the maintenance of attentional control. Deficits in maintaining attentional control manifest as inconsistent intra-individual performance on sustained attention tasks with periods of normal performance and other periods of poor performance thought to reflect "inattention", and considered by several groups to be an important component of ADHD. Such lapses in attention would result in the common finding of fluctuations in reaction time (intra-individual RT variability), which we find in our NAT performance measures, recently characterized as infra-slow frequency oscillations. A logical step in relating these performance fluctuations to brain processes is to examine large-scale brain networks known to have similarly infra-slow fluctuations in activity. There is fMRI evidence for decreased coherence within the default network and less suppression of default network activity during external tasks in ADHD. Given the putative relationships between default network and attentional control networks, these results suggest there may be alterations in attention control networks as well. Hence, investigation of possible changes in slow fluctuations in attention control networks and their relationship to attentional lapses in ADHD, and emphasizes the need for intra-individual measures of brain processes over time to characterize the neural fluctuations of attentional control during sustained attention.

Cognitive neuroscience studies have clearly identified two functional, and neurally distinct, components of attentional control: top-down controlled enhancement of attended targets and top-down controlled suppression of ignored distractors. Subjective assessments indicate distractability to be a key factor in ADHD, and a recent objective study has demonstrated that individuals with ADHD have a deficit in the recruitment of attentional control over target processing and suppression of distractors. While the latter study used behavioral measures, it has been shown that patients (elderly with cognitive decline) can be differentiated on the basis of fMRI-based brain measures of distractor suppression versus target enhancement, demonstrating that these separate top-down control systems can be altered independently as well. This implies a need for intra-individual measures of brain processes over time to characterize maintenance of both processes: attending targets and ignoring distractors. Objective assessment tests must obtain brain measures of both components of attentional control and their intra-individual fluctuations during sustained attention. Detecting fluctuations over time requires continuous measures of both target and distractor processing. Doing so improves diagnostics and monitoring of the brain effects of treatment.

Unlike any other behavioral or EEG-based assessment methods of ADHD, our Neurophysiological Attention Test (NAT) utilizes a novel EEG method to measure infra-slow fluctuations in BOTH attending and ignoring simultaneously during sustained attention tasks.

The NAT is the first EEG-based method for continuously tracking neurophysiological indices of attending targets and ignoring distractors simultaneously during sustained attention tasks. We adapt the steady-state visual evoked potential (SSVEP) method to take advantage of the fact that the magnitude of stimulus processing in sensory cortex (measured by the SSVEP) provides an index of attentional top-down control from frontal-parietal systems. Our method makes it possible for the first time to continuously measure the intra-individual variability (infra-slow fluctuations) of electrophysiological brain activity representing the top-down controlled processing of BOTH attended targets and of ignored distractors in ADHD. Measurements of infra-slow fluctuations can also be fMRI-based.

Our innovation is to use the time-proven SSVEP frequency tagging measures, and for the first time in a continuous mode to track infra-slow fluctuations (~0.1-0.02 Hz) in control over both sustained attending and sustained ignoring throughout continuous attention tasks (FIG. 1). To do this we measure activity reflecting the processing of two different stimuli (target and distractor) concurrently. However, it is challenging to define EEG measures that can be used unambiguously to measure the responses to each of multiple stimuli presented simultaneously. The SSVEP frequency tagging method allows the attended target signal and the ignored distractor signal to be identified by the frequency of the SSVEP. Each stimulus type (target, distractor) is assigned a flicker frequency (e.g., 15, 17 Hz respectively) that drives visual sensory cortices at the flicker frequency of each stimulus, thereby isolating and stabilizing the EEG activity corresponding to each stimulus type even when they are presented at the same time or even in the same location, e.g. in figure/background configuration. It is the infra-slow fluctuations in attending and ignoring that one can be aware of (meta-attention), and thus these measures can be used for assessment of meta-attention and for feedback about attending and ignoring and training meta-attention to improve attentional control. Many patients, for example those with ADHD, stress, anxiety and depression, have less meta-attention, i.e. they are less self-aware of their attention, or are less frequently self-aware of their attention. This results in negative symptoms and decrement of quality of life. Improving their meta-attention and thereby also their attentional control can greatly benefit these patients.

The NAT also provides behavioral performance data during the sustained attention task. Our findings from the NIH award are consistent with the literature on altered intra-individual reaction time variability, showing increased ultra-slow fluctuations in reaction time (0.05-0.1 Hz) in ADHD (see Appendix A). In this NIH Small Business Innovation Research Award we showed that the combination of our behavioral and electrophysiological measures was better than the current gold standard assessment method (Conners CPT test) for diagnosis of ADHD.

In accordance with the embodiments of the present invention, in addition to relating physiological indices to performance, the physiological indices themselves have functional significance. In fact, they can uncover important brain function differences, in the presence of similar behavioral measures, that can be differentially targeted by therapeutics. At a minimum, they can provide additional, otherwise unavailable, information to behavioral measures that may not completely differentiate sub-groups of patients (but suggest that there may be sub-groups), to aid in that differentiation.

This represents both significance and innovation because it will impact the field (significance)—drive development of new therapeutics; and its novel/innovative approach will impact thinking in the field and is expected to generate new lines of research and development of new types of therapeutics. The method not only significantly improves assessment and therapeutics; but it can open the door to new categorization of individuals and patients, and to the development of a new line of therapeutics.

One good example of how suppression of distractors is important is, if you do not suppress distractors well, then they get into working and short term memory and interfere with long-term formation of memories for relevant information, and contribute to confusion. It is likely that less suppression of distractors could lead to shifts in attention away from relevant information. There are multiple cognitive disorders where this type of problem is a contributing factor and it impacts performance and well being in everyone.

Five key advantages include: (1) Capability to measure fluctuations in performance continuously over time to track performance-related aspects of sustained attention. (2) Capability to simultaneously and continuously track a physiological index of the attended channel of information during the task, and (3) the physiological index of the ignored/distractor channel of information. (4) Capability to relate the indices for the attended and ignored channels of processing to each other and to performance. (5) Capability to provide feedback about these indices to the user.

Decomposing the physiological/functional components contributes to performance. Performance can be decomposed into attention related enhancement of target processing and distractor suppression contributions.

In addition, these performance measures do not disrupt and re-set attention like CPT tasks that utilize no-go stimuli (e.g., Conners CPT; SART). Note that mental drifting is disrupted and attention is thereby re-set in terms of RT when a rare no-go stimulus occurs within a go/no-go task. However, by disrupting natural attentional drift, one greatly diminishes the ability to continuously track natural waxing and waning of attention.

The major advantages of these methods are that they measure both attention related processing and distractor processing directly (not inferred), simultaneously, and continuously. In addition, the same measures are used for both attended processing and distractor processing, i.e. there are not two different types of measures, consequently, and comparison between these two key attention functions is more direct.

Direct measures of distractor processing: Direct measures of distractor processing provide a more accurate assessment of how distractors are being processed, than indirect methods such as inferring their level of processing from their impact on target processing. In addition, the impact on target processing and attention-related processes can also be analyzed.

Simultaneous: Measuring (the allocation of resources to) both attending and ignoring in parallel makes it possible to accurately monitor the effects of fluctuations in arousal and control upon both attending and ignoring. It also makes it possible to assess the relationship between changes in attending with respect to ignoring.

Continuous: Not interrupted by probes or other rare events that tend to reset attention, thereby obtaining more natural data on the waxing and waning of sustained attention. Additional assessment tools may add probes or different types of continuous tasks as well.

In some embodiments, SSVEPs serve as indices of target and distractor processing. These measures are employed to reflect processing of relevant (target) and irrelevant (distractor) information.

This protocol leverages an EEG sensing method (SSVEPs) to provide two important key advantages for functional measures of attention: (1) provides continuous electrophysiological tracking of sustained attention with high temporal resolution; and (2) provides continuous tracking of the levels of BOTH attention to targets and suppression of distractors simultaneously, as well as performance on a CPT task.

Steady State Visual Evoked Potentials (SSVEPs) are EEG measures of the signals from cortical brain regions that respond in synchrony with a flickering visual stimulus, the signals represent brain responses that have reached a steady-state relationship with visual stimulus. Frequency Tagging uses more than one stimulus, each stimulus flickering at a different frequency, so that a particular frequency is an index of that stimulus. Similarly, the SSVEPs at each frequency are an index of the brain response to the stimulus flickering at that frequency. This allows us to "Tag" a brain response as being an index of the brain processing of a specific stimulus in the visual scene. For example, one visual stimulus can flicker at 15 Hz and serve as the stimulus to be attended in our task, and the other, distractor stimulus (to be ignored) can flicker at 20 Hz. By recording the SSVEPs at these two frequencies (15 Hz and 20 Hz) we have brain electrophysiological indices of the amount of brain processing of the attended target stimulus (15 Hz SSVEP) and the ignored distractor stimulus (20 Hz SSVEP).

Using SSVEP to compute attention can be implemented by presenting faint marker stimuli that flicker on the screen and to superimpose upon the marker stimulus other stimuli that serve as the content for the task. For example, on a light grey background dark grey circular patches can be presented on the left and right of fixation, flickering at 15 and 20 Hz, respectively. Superimposed upon these two patches can be red letters (or other characters) at a rate that is typical in an attention task, e.g. one per second, and the subject is asked to attend to the letters in the left circular patch and ignore the letters in the right circular patch. Note that the signals of interest are the two SSVEPs coming from the two patches, not the small transient responses to the red letters. Additional assessment tools may use single trial analyses of transient responses to targets and distractors and their changes over time as well.

Attention causes the SSVEP to be much larger when the flicker patch location is attended than when it is ignored. This exemplary method is more effective than transient (brief) attention modes. That is, short time epochs (typically about 1 second) are extracted from the attention task and then signal averaged to obtain the average signal magnitude for the stimulus when it is attended and for that same stimulus when it is ignored. That is, the continuous data are broken into short epochs that are then signal averaged. This provides an improved signal to noise ratio, but eliminates all the information about any differences in the SSVEP at different times during the task, i.e. the slow fluctuations in attending and ignoring. Also, using many short intervals of task performance (e.g. 5-30 seconds at a time) are typically used specifically to avoid fluctuations in ability to pay attention that arise when one has to sustain attention for more than 30 seconds. Consequently, short time epochs explicitly do not measure the differences in attention level (or distractor processing level) that are thought to occur when one pays attention and ignores distractors for extended periods of time, i.e. they do not measure the properties of sustained attention.

In this exemplary protocol, sensors SSVEPs employs circular patches of stimuli at an attended and ignored location, and records these signals continuously during extended 4 minute runs of sustained attention. Tracking the magnitude of the signals for both the attended stimulus (attending/target magnitude) and the ignored stimulus (ignoring/distractor magnitude) continuously over the 4 minute runs is accomplished by taking the filtered 15 Hz and 20 Hz SSVEP signals and obtaining the Hilbert transform of the signals over the 4 minute run. The results have shown two novel findings that fit with models of attention. First, the attended signal and the ignored signal both fluctuate dramatically (e.g. on the order of 100% amplitude fluctuations) over time periods in the range of 10-30 seconds consistent with the waxing and waning of sustained attention, and demonstrates that there are robust data to work with. Second, the fluctuations of the two signals are not necessarily in synchrony—this demonstrates that attending and ignoring are separable processes. The latter point means that these measures can be used in principle to track peoples' ability to sustain attention and to sustain ignoring distractions simultaneously. This is the basis for the described diagnostic categories, and styles of attending/ignoring in non-patients, and for subsequent development of new therapeutics and enhancement methods to target the new categories of attention disorders and attention styles.

The use of SSVEPs to measure slow fluctuations enables the devices for the method to be produced inexpensively and used by anyone (i.e., not requiring knowledge of EEG recordings) so that individual consumers can readily purchase and use them. This broadens the use of the method beyond research, educational and clinical facilities to individual consumers. This has great impact on assessment of attention control and the consequent creation of new categories of patients and clinical disorders. Nearly all other types of clinical assessments are performed in the clinic greatly limiting the view of the patient's condition/disorder. Performing assessments in real life conditions improves the characterization of the patient's condition and is expected to lead to much more personalized assessments and to creation of new categories of clinical diagnosis. Accessibility to individual consumers also makes it possible to use the method for monitoring treatment effects in everyday life contexts, greatly improving accuracy of tailoring treatment to the individual patient. It also makes it possible for patients and non-patients to use the method to improve their attentional awareness and attentional control by training any time and anywhere rather than being limited to a facility for training (e.g., clinic, school, health spa).

In some embodiments, the target/distractor stimulus parameters and task have been developed through pilot tests to create sufficiently distracting distractors, i.e. they create qualitative experientially salient interference to participants. The goal is to have stimulus parameters that create enough difficulty and distractor interference that a slight increase in distractor salience (brightness or duration) produces a decrease in accuracy. This ensures that there is a benefit to suppressing distractors—if the target discrimination is too easy, and/or the distractors are not sufficiently disruptive, then there is little need to suppress distractors. 2) We prefer difficulty level to be substantially at 100% accuracy, such that any waning of attention or decrease in distractor suppression will result in a loss in accuracy. This protocol adjusts target and distractor brightness and duration to determine the stimulus parameters that produce the desired cognitive effects. Note the stimulus parameters (other than position) are equal for target and distractor so that the stimuli do not produce unequal brain responses.

Why not just use EEG alpha-band measures or fMRI? The same type of measurements could be performed with fMRI approaches in principle, however, it is not known if the signal magnitudes would be large enough for evaluation of individual patients and the cost would be prohibitive (on the order of $1,000 per person) and the assessments would be limited in number (due to expense) and not be available in real world conditions. These methods are an advance or improvement over using alpha-band recordings for which it is difficult to identify which signal corresponds to the attended vs. ignored stimulus, and the magnitude of the alpha signal may not be large enough for real-time monitoring. With alpha it is difficult to use anything other than two widely separated stimuli (so only spatial location can be used as an index; and can be difficult to differentiate the responses to task stimuli from other alpha sources). This method may be extended to examine both the stimulus driven system of attending/ignoring and other systems related to waxing and waning of arousal etc. that would be reflected by naturally occurring alpha simultaneously. It may also be possible to develop other configurations of stimuli, including foreground vs. background; superimposed stimuli; auditory stimuli; effects of contextual information, etc. none of which can be used effectively with alpha measures.

Figure 1B:
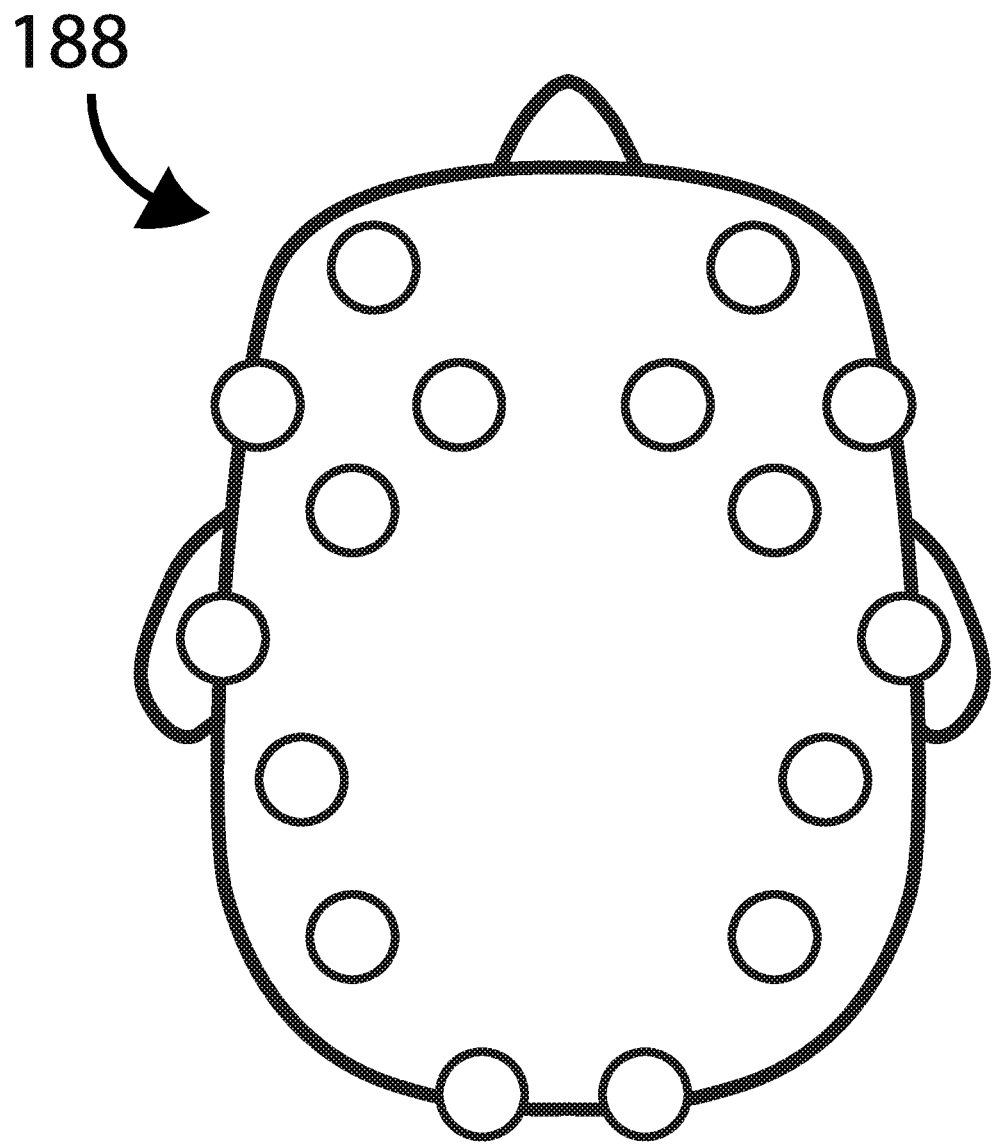
FIG. 1B is a top view of a user's head with exemplary locations for measuring SSVEP and/or SSAEP.

In one exemplary embodiment, as illustrated by FIG. 1A, an attention evaluator and/or trainer 100 includes a computerized processor 150, an output device 152 (e.g., video display with speakers), an input device 154 (e.g., keyboard, mouse, touchpad, and/or joystick) and a neural scanner 156 (e.g., headgear with EEG sensors) operatively coupled to the head 188 of a user 180. FIG. 1B is a top view of head 188 showing a plurality of exemplary locations for scanning SSVEP (Steady State Visual Evoked Potentials) and/or SSAEP (Steady State Auditory Evoked Potentials).

Figure 2:
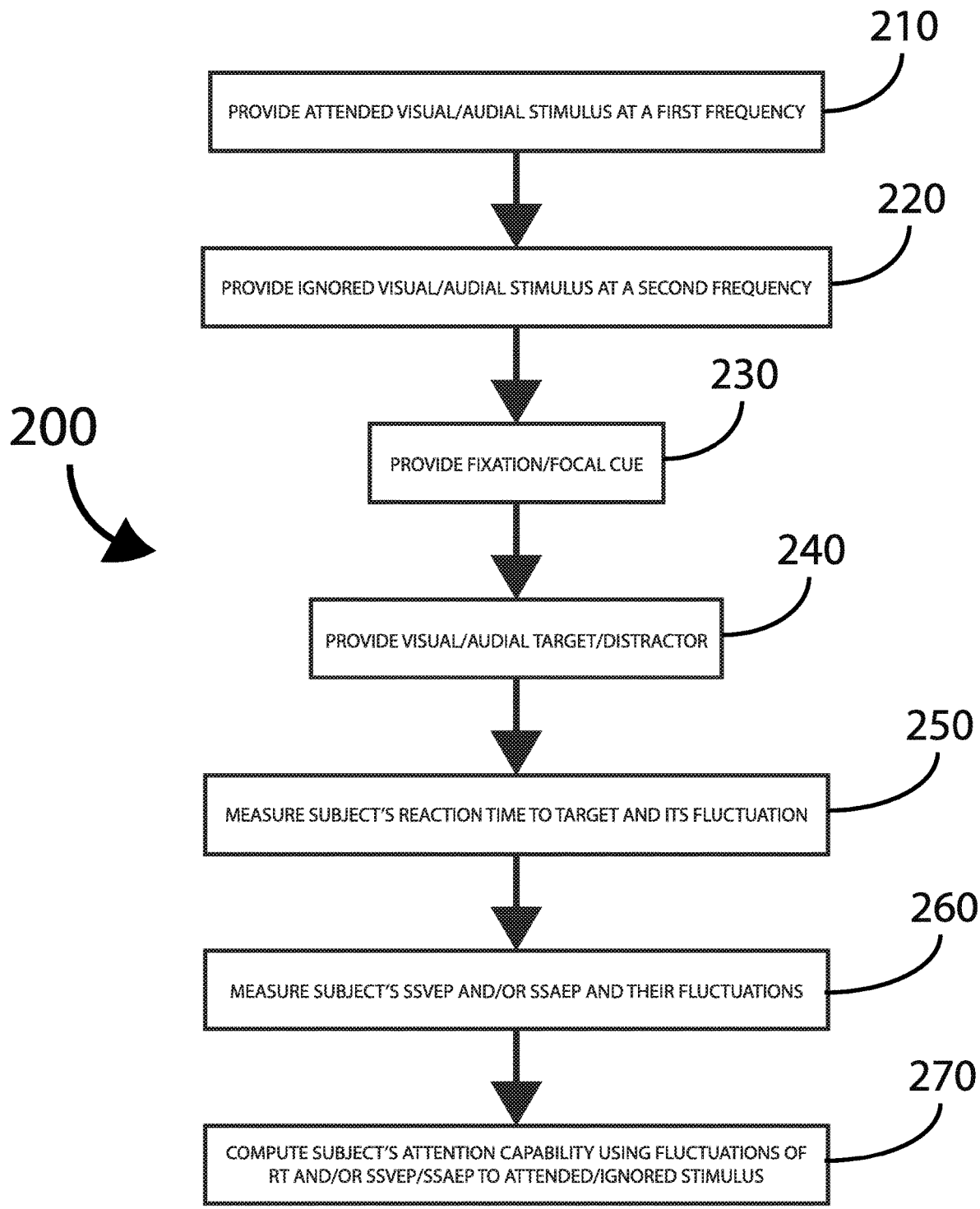
FIG. 2 is a flow diagram of an exemplary testing protocol for the embodiment of FIG. 1A.
Figure 3A:
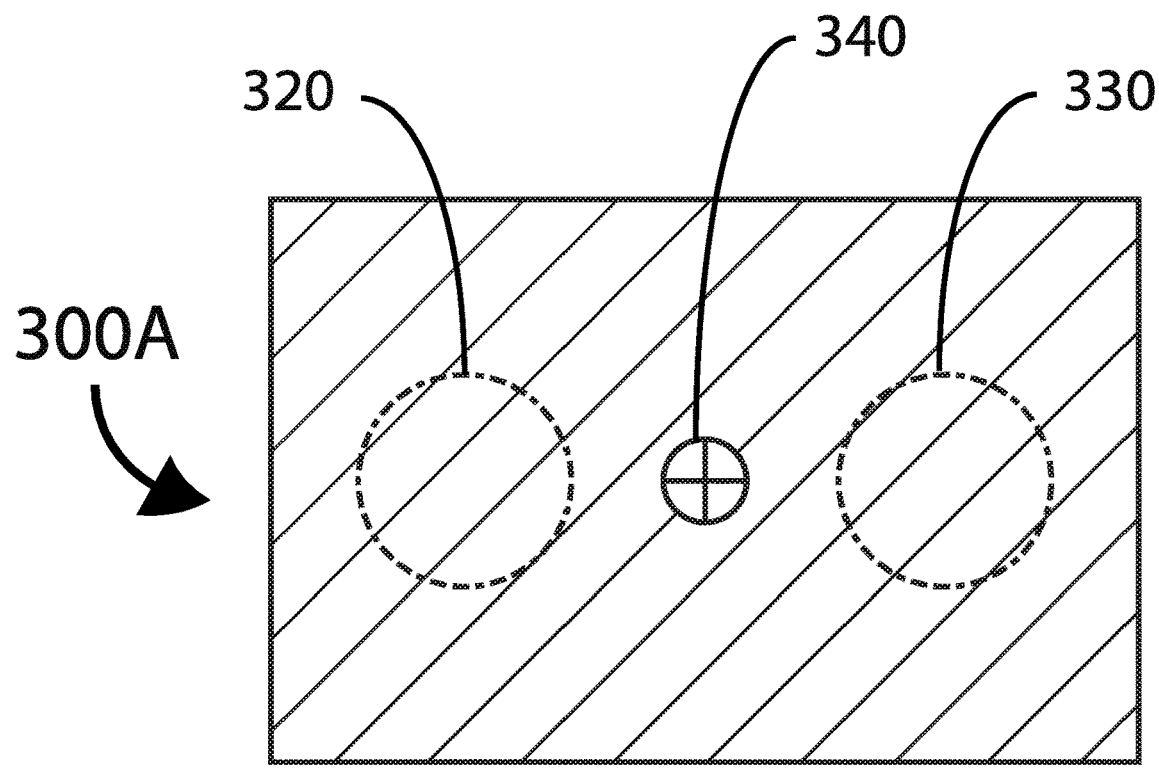
FIGS. 3A-3C and 4A-4C are screenshots illustrating exemplary protocols for the embodiment of FIG. 1A.
Figure 3B:
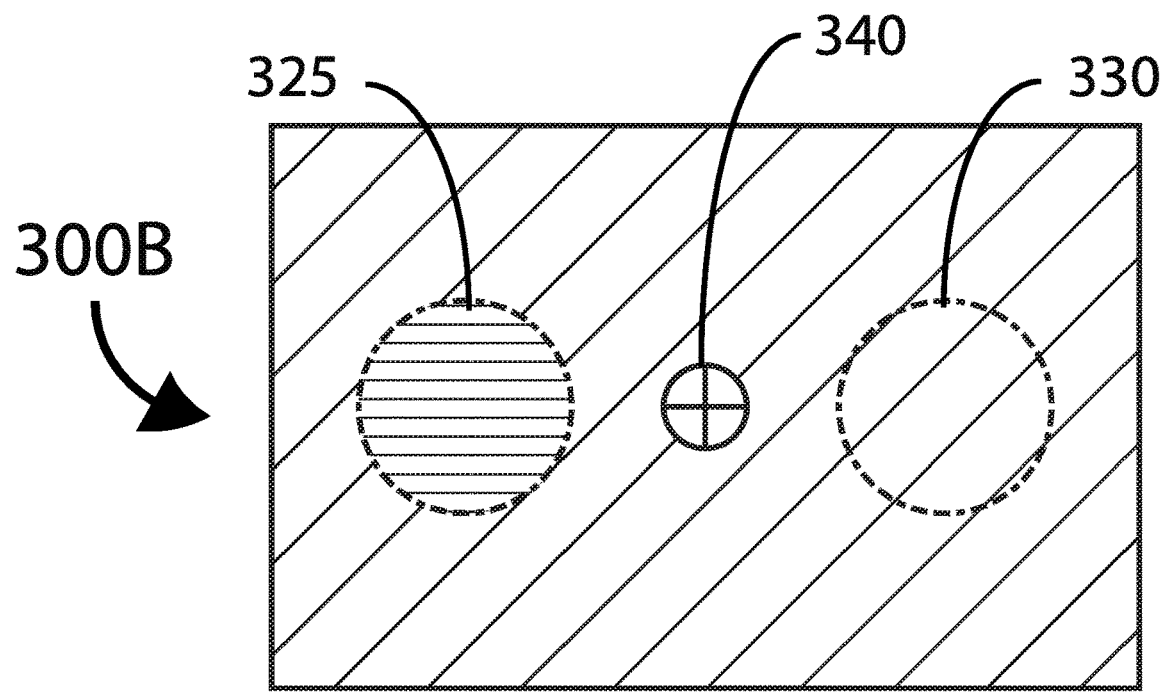
Figure 3C:
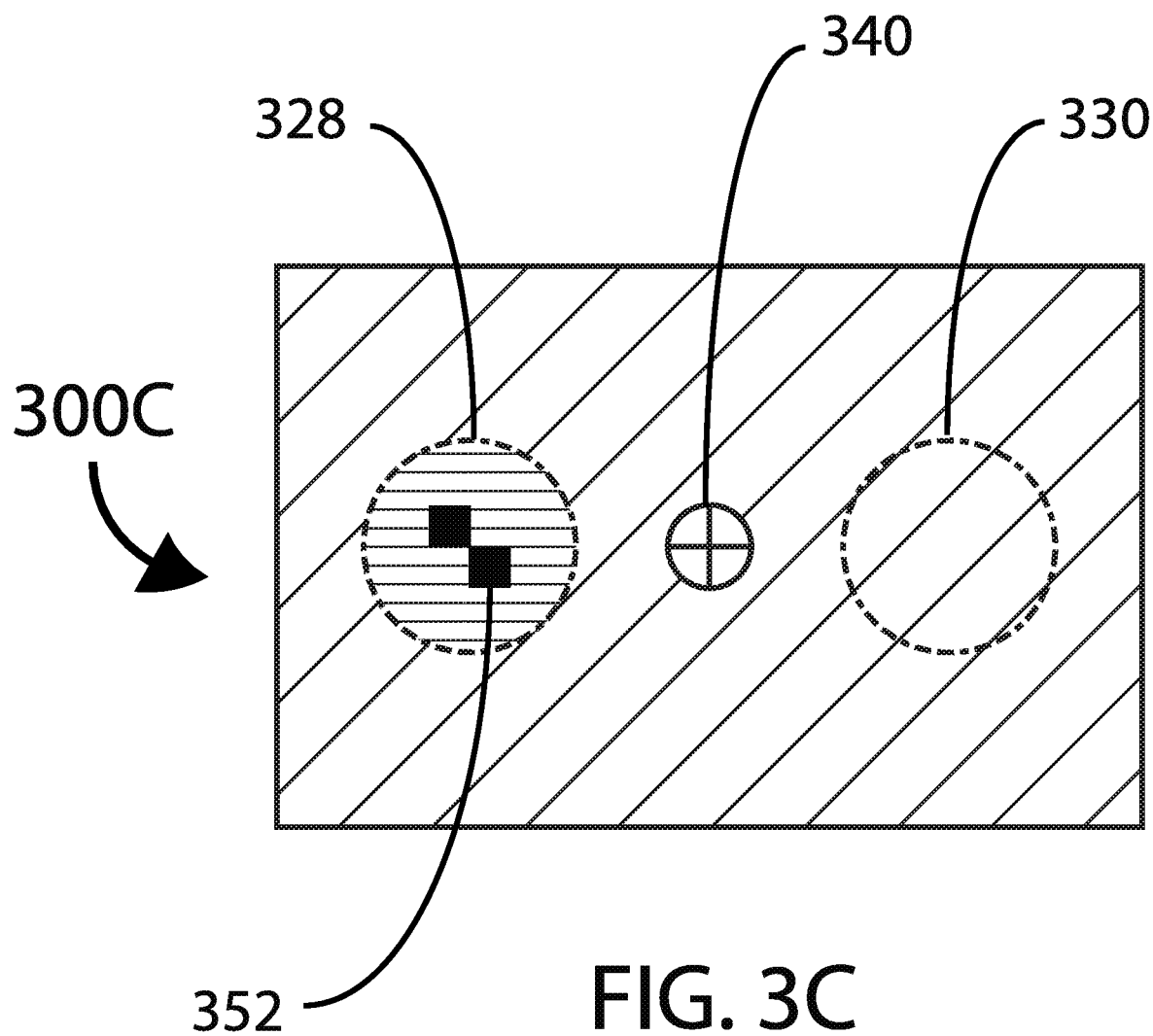

Referring initially to the screenshots 3A and 3B, FIG. 2 is a flowchart 200 illustrating an exemplary attention assessment protocol, using an attention evaluator and/or trainer 100, useful for accessing attention capability or deficits thereof such as ADHD.

In step 210, output device 152 presents and instructs user 180 to attend to a first visual and/or audial (also referred to as "auditory") stimulus, such as a visual circle (also referred to as "circular patch") alternating between lighter circle 320 and darker circle 325, and flickering at a first frequency, generally approximately between 3 Hertz and 40 Hertz, and preferably substantially between 15 Hertz and 18 Hertz.

Figure 4A:
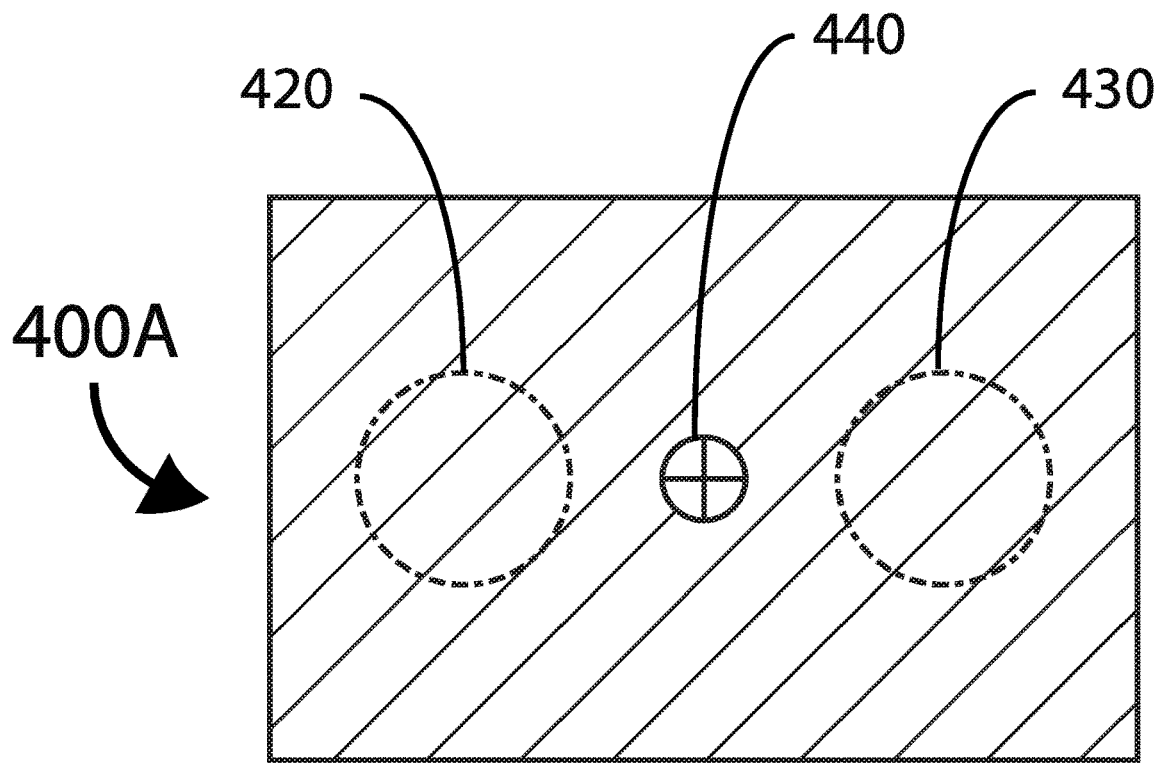
Figure 4B:
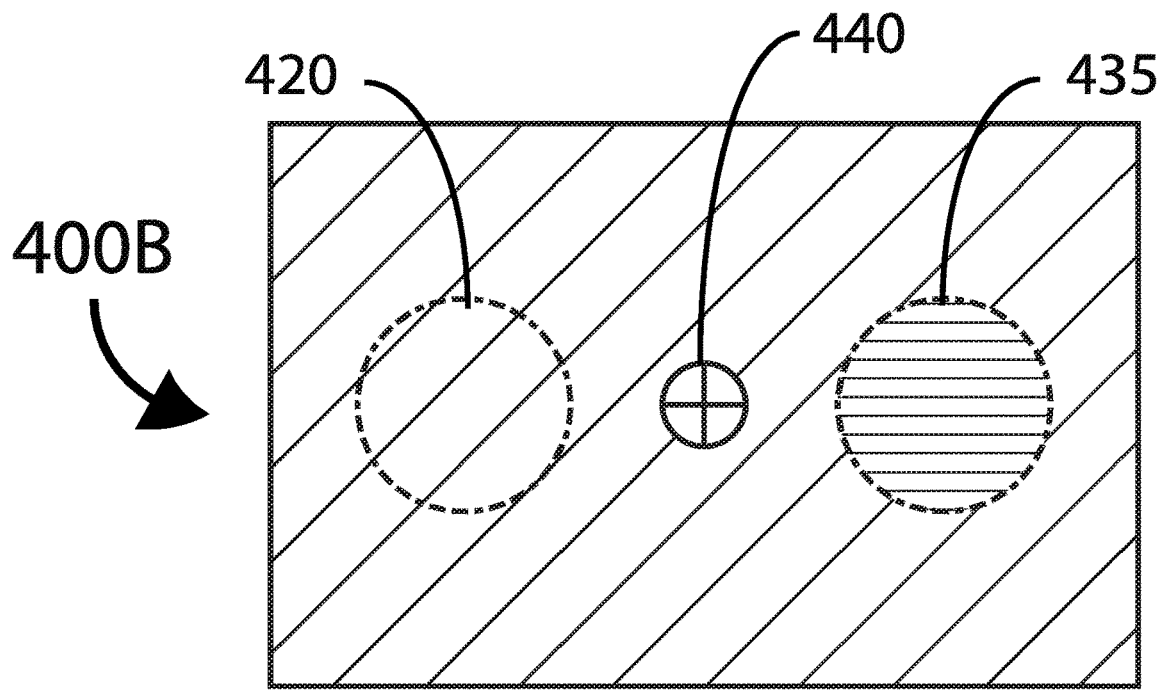
Figure 4C:
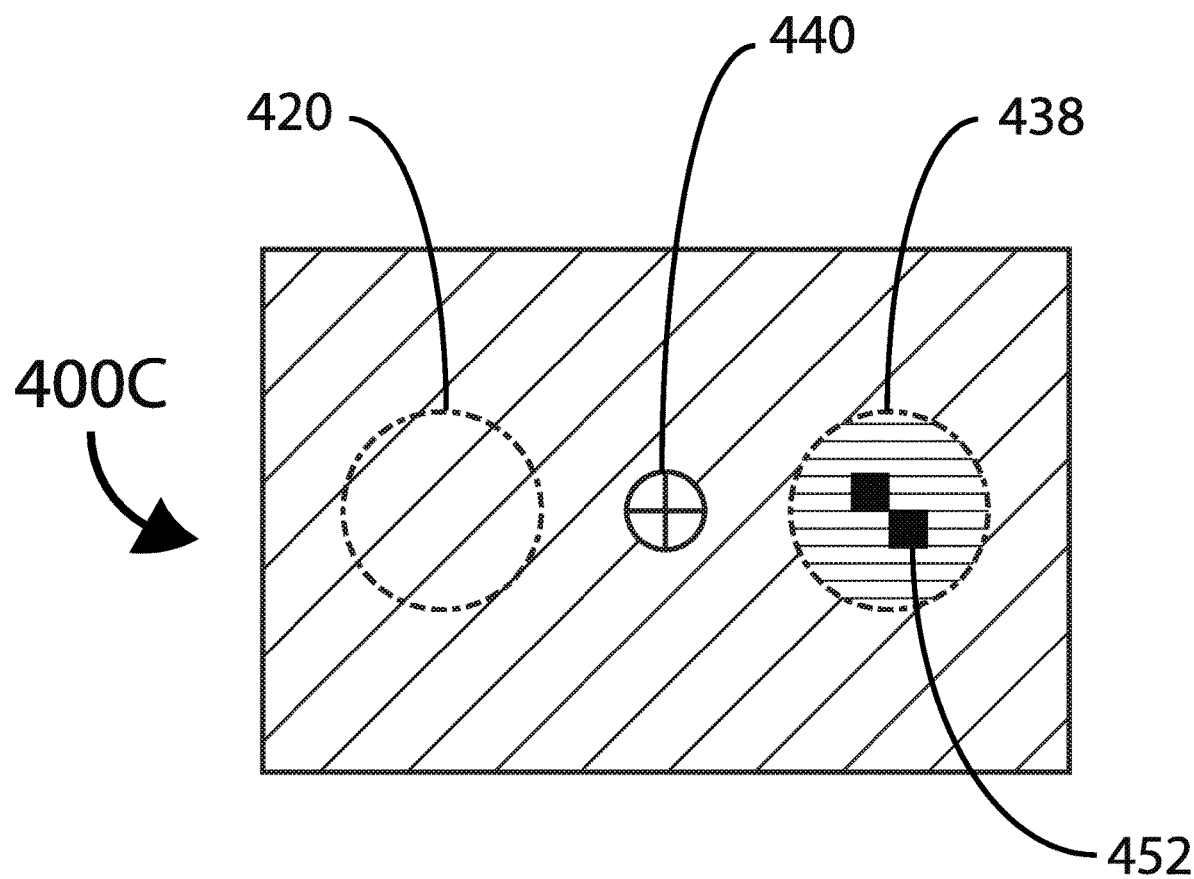

Referring also to the screenshots of FIGS. 4A and 4B, output device 152 also presents and instructs user 180 to ignore a second visual and/or audial stimulus via output device 154, such as another flickering visual circle alternating between lighter circle 430 and darker circle 435, and flickering at a second frequency, generally approximately between 3 Hertz and 40 Hertz, and preferably substantially between 15 Hertz and 18 Hertz (see step 220).

In step 230, user 150 may also be provided with an optional suitable focal cue, such as to focus user's eyes on fixation point 340. In this example, the first flickering frequency can be 12 Hertz and the second flickering frequency can be 16 Hertz, and the fixation point 340 can be located approximately midway between the attended circle 320 and the ignored circle 330.

In some embodiments as illustrated by the respective screenshot 300C and screenshot 400C, a randomized plurality of targets and/or distractors, e.g. target 352 and/or distractor 452, can be presented to user 180 either in attended circle 328 and/or ignored circle 438 (step 240). Presentation frequency of targets and/or optional distractors can be approximately between one and five seconds, and can be randomized with respect to presentation rate, location and/or duration. Although squares are used for targets/distractors in this embodiment, other shapes are also possible, e.g., circles, ovals, rectangles, polygons, triangles or any other regular or irregular shapes.

The user is instructed to respond to target(s) and to ignore any distractor(s). Processor 150 optionally computes fluctuation of user's reaction time to the targets, e.g., target 352 (step 250). Reaction times can be measured using input device 154.

Neural scanner 156 measures the user's SSVEP and/or SSAEP (step 260). Neural scanner 156 can be an EEG headset such as the EPOC™ available from Emotiv of San Francisco, Calif. and EEG headset available from Imec of Lueven, Belgium.

In step 270, processor 150 computes the user's attention capability using the fluctuation and/or SSVEP/SSAEP using the above described protocol. The computed capability can be provided to the user and/or a human therapist for evaluation purposed, and hence can be used for development of a personalized treatment plan.

This can be computed by frequency tagging, e.g., using a moving window fast Fourier (FFT) of the EEG to extract the magnitude (e.g., amplitude) of the SSVEP signal over time, thereby yielding a waveform that includes the infra-slow fluctuations of the SSVEP magnitude over a sustained period of time (e.g., from about five seconds to about two minutes, preferably approximately between 10 seconds and 100 seconds). Note that the "raw" SSVEP signal includes measurable representations of the above described flickering frequencies.

The FFT of the waveform can be used to compute the magnitude of the ISF in an exemplary frequency band (such as 0.01-0.2 Hz). The infra-slow fluctuations of the extracted SSVEP can be used to compose an attention score which is useful for example diagnosing ADHD.

This technique results in an attention score that aids clinicians in their assessment of an individual's capacity to attend and ignore inputs, in simple form, for example:

A(sub ignore)=Power (infraslow band over time)
A(sub attend)=Power (infraslow band over time)
A(sub performance)=Power (infraslow band over time)
Wherein A is the attention score for each.

These techniques can be summarized by the exemplary equations:

$$A_I = P_I(t)_{ISF} \qquad \text{EQUATION A}$$

$$A_A = P_A(t)_{ISF} \qquad \text{EQUATION B}$$

$$A_P = P_P(t)_{ISF} \qquad \text{EQUATION C}$$

Wherein:
A=attention score (indicate sub-I=Ignore; sub-A=Attend; sub-P=Performance)
ISF=InfraSlow Fluctuations—very low frequencies, such as from 0.01-0.2 Hz.

P(t)=Power over time for the infraslow frequencies

NOTE: The magnitude of the power can be found using a FFT, wavelet or other type of transform.

Other modifications and additions are also possible. For example, the magnitude of the waxing and waning of attention reflected in the ISF magnitude can also vary over tens of minutes and hours of the day, or across days or longer periods which can be measured with the ISF magnitude at different periods.

Alternatively or in addition, a new measure that combines the ISF with other EEG measures can be created by relating the ISF to other EEG measures extracted at the same time. For example frontal activity could be found that co-varies with the ISF.

Many other modifications and additions are also possible. For example, it may be possible to present targets substantially outside of the attended area, and identify the targets using a color, a shape or an alphanumeric character (or any suitable symbol such as an Arabic character or Chinese calligraphic symbol).

There are also alternate methods for explicitly and/or implicitly incorporating a target with the attended area, such as superimposing a "target" onto the attended area, by, for example, substantially lengthening/narrowing the duration of the flickering pulse and/or varying the color, shape and/or size of the attended area.

Figure 5:
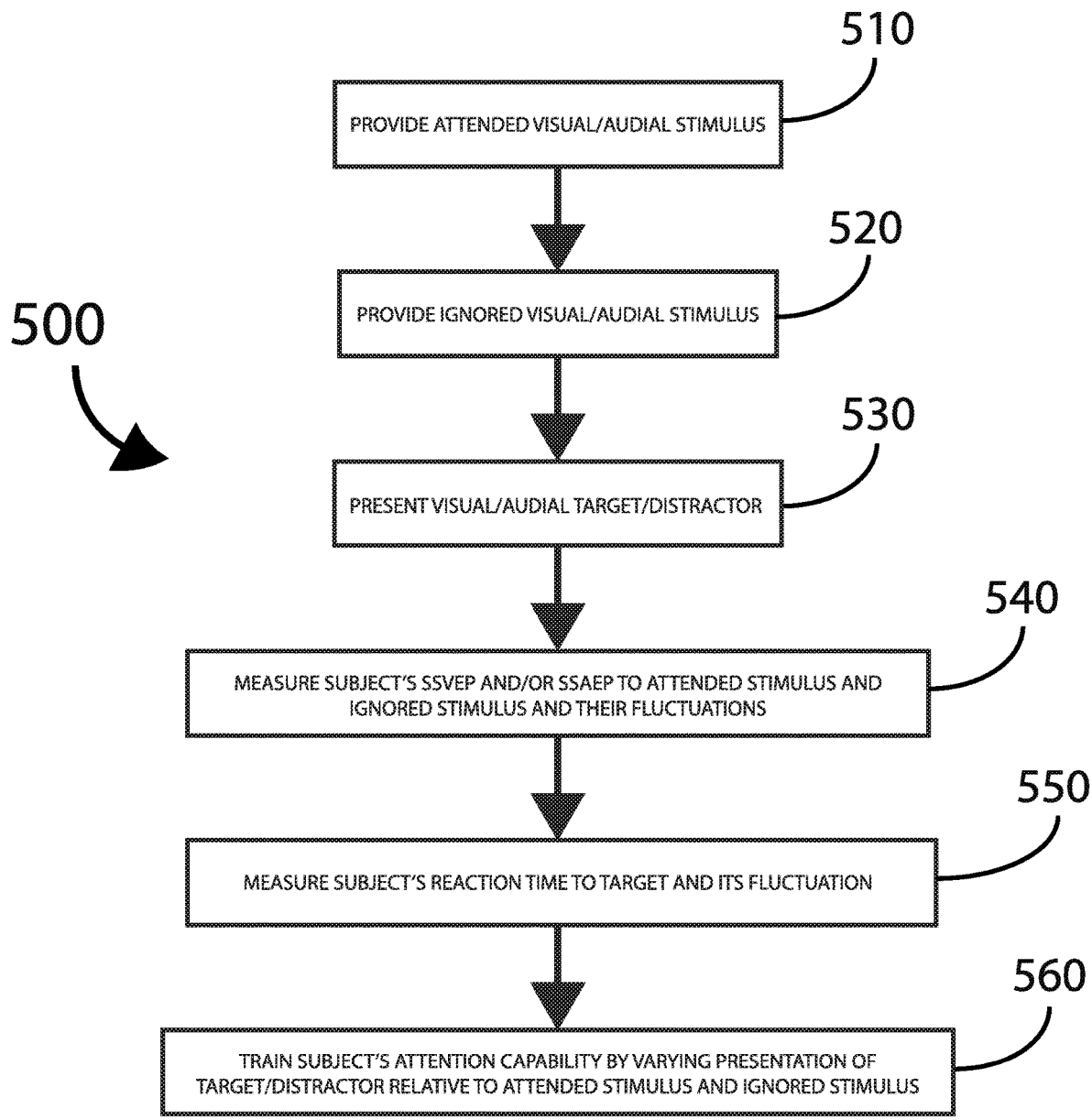
FIG. 5 is an exemplary flow diagram of an exemplary training protocol for the embodiment of FIG. 1A.

Referring now to the flowchart of FIG. 5 and the screenshots of FIGS. 3A-3C & 4A-4C, attention evaluator and/or trainer 100 can be adapted to provide both diagnosis and treatment protocols.

In some protocols, as illustrated by step 510, output device 152 presents and instructs user 180 to attend to a first visual and/or audial stimulus, such as a visual circle alternating between lighter circle 320 and darker circle 325, and flickering at a first frequency, generally approximately between 3 Hertz and 40 Hertz, and preferably substantially between 15 Hertz and 18 Hertz.

Output device 152 also presents and instructs user 180 to ignore a second visual and/or audial stimulus via output device 152, such as another flickering visual circle alternating between lighter circle 430 and darker circle 435, and flickering at a second frequency, generally approximately between 3 Hertz and 40 Hertz, and preferably substantially between 15 Hertz and 18 Hertz (see step 520).

In some protocols, user 150 may also be provided with a suitable focal cue, such as to focus user's eyes on fixation point 340 located approximately midway between the attended circle 320 and the ignored circle 330.

As illustrated by screenshots 300C & 400C, a randomized plurality of targets and/or distractors, e.g., target 352 and/or distractor 452, can be presented to user 180 either in attended circle 328 and/or ignored circle 438 (step 530). Target(s) and/or optional distractor(s) are generally present between approximately one and five seconds, and can be varied with respect to presentation rate, location and/or duration, depending on the training protocol(s). Although squares are used for targets/distractors in this embodiment, other shapes are also possible, e.g., circles, ovals, rectangles, polygons, triangles or any other regular or irregular shapes.

In steps 540 and 550, neural scanner 156 measures the user's SSVEP and/or SSAEP, and the user's reaction time to the distractors may also be measured. Processor 150 can compute the user's attention capability derived from the SSVEP and/or SSAEP, and/or the fluctuation of user reaction time.

In one exemplary "executive function" training protocol as illustrated by step 560, the presentation of the target(s) and/or optional distractor(s) relative to the attended and ignored stimuli are varied to either draw the user's attention towards and/or away from the attended/ignored stimuli. This can be accomplished by, for example, repeatedly displaying targets(s) and/or optional distractor(s) at one or both of the attended stimulus and ignore stimulus, while monitoring the reaction time and/or accuracy of the user's response to the distractor(s).

Figure 6:
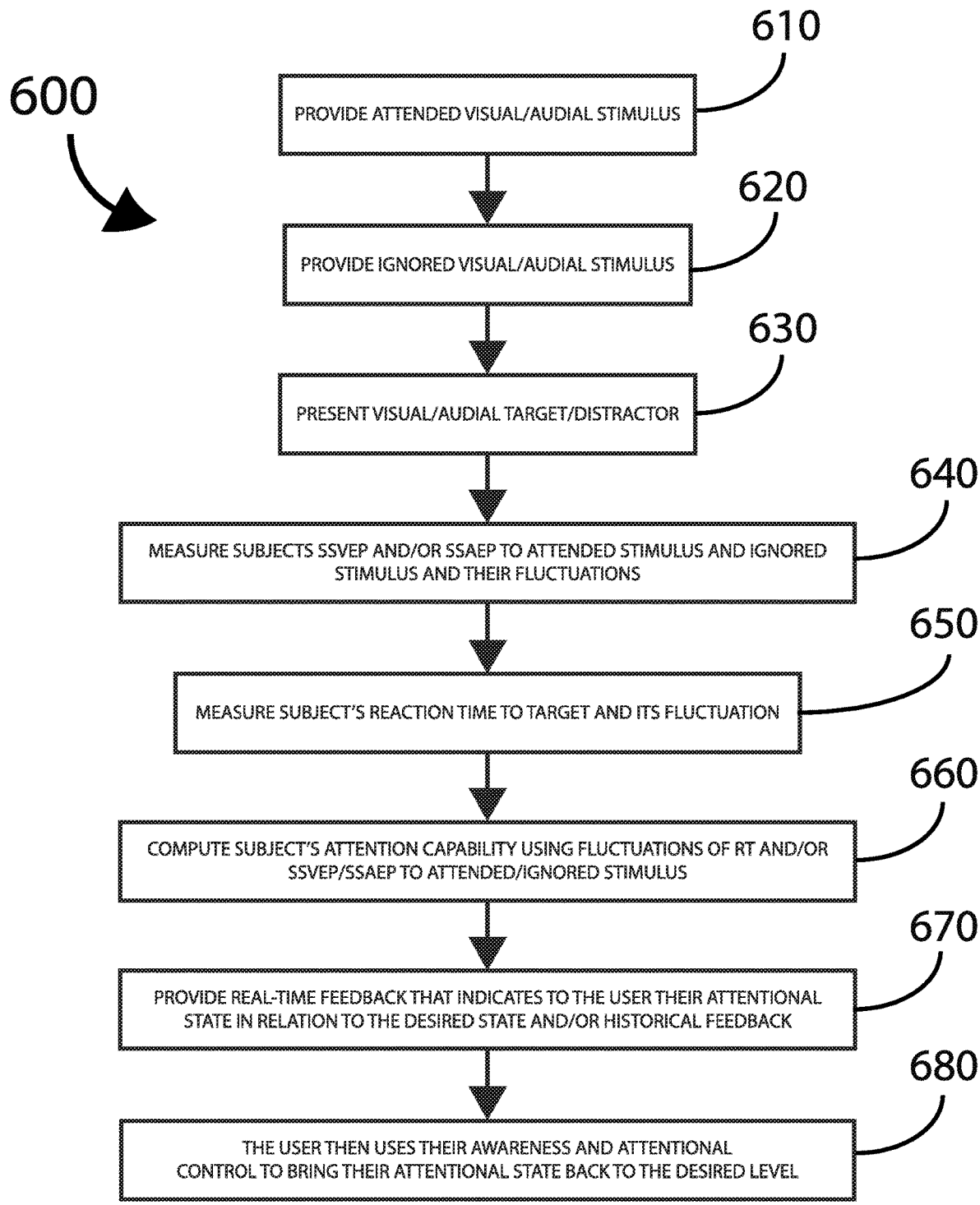
FIG. 6 is another exemplary flow diagram of a second exemplary training protocol for the embodiment of FIG. 1A.

In a modified exemplary "meta-attention" training protocol as illustrated by step 670 of FIG. 6, the subject is provided with real-time feedback about their attending or ignoring level based upon their SSVEP/SSAEP to the attended or ignored stimulus (respectively), and the subject then learns to be aware of their attending or ignoring level, increasing their attentional awareness; the subject then brings their attending or ignoring level back to the desired level (step 680), thereby learning how to control their attentional processes. With repeated use, the subject learns how to control their level of attending or ignoring. In other instances, meta-attention training can be accomplished by feedback provided at the end of a session (historical feedback) to teach the subject how to be aware of what their attending or ignoring was like through retrospective self-reflection. For example, if a subject is presented with a salient distraction during the sustained attention task (e.g., an emotional stimulus), it will capture the subject's attention and there will be a period of time needed to bring their attention back to the task that will be reflected in the SSVEP/SSAEP level. At the end of a training session on the sustained attention task, the method (670) will provide feedback by illustrating how long it took to recover their attention level in the attention task each time a salient distractor occurred. By reflecting on those feedback data, the subject learns about their attentional control and becomes more aware of their attention (improved meta-attention) and can then repeat the task with heightened awareness to learn better control. Repeated usage (steps 610-680) can be used to increase the subject's attentional awareness and train them to improve their level of attentional control over attending and ignoring.

Modifications and additions to the above embodiments are also possible. For example, in some protocols, the flickering pulse width, intensity and/or color of the attended/ignored area(s) can be varied for the purpose of drawing attention to and away from attended area and/or ignored area. Alternatively or in addition, size and/or shape of the attended/ignored areas may be varied for the same purpose. Alternatively, non-spatial differentiation of the attended and ignored stimulus information can be used, for example natural scenes where objects appear without fixed location and one type of object is attended and another type or class of object is ignored, where the non-spatial properties of the objects determine their type/class (e.g., color or shape or texture). Another example of non-spatial features that can be used to differentiate attended and ignored stimuli is motion. For example one class of moving object (which could include an avatar controlled by the subject) is attended, but other moving objects are ignored. Sensory modality (e.g., auditory, visual) can be used as a non-spatial feature for differentiation. For example, subjects could attend to visual objects while ignoring sounds.

Alternatively or in addition, conjunctions of non-spatial and/or spatial properties can also be used to define attended and ignored stimuli, for example scenes in which the background is ignored and the foreground is attended; faces that are speaking (visual and auditory) in the left visual field (spatial) are attended and faces speaking in the right visual field are ignored, or faces that are speaking about one topic are attended and faces speaking about another topic are ignored. Consequently, an enormous range of stereotyped or realistic stimuli can be used to create desired attentional tasks and cognitive loads, thereby providing a large range of assessment and training environments that can be related to everyday life activities. These can include attention tasks in which the subject builds awareness of control over when and what to attend to out of multiple stimulus sources.

Meta-attention or awareness of attention includes the capability to search and identify where your mind is (which external input or internal process is being attended or ignored). The training teaches how to have better awareness of attention (better at searching and identifying) leading to better control of attention. If attention is on the task, then keep it there, if it has been captured by a distraction, then bring it back to the task. Alternatively or in addition, there can be primary and secondary channels of information and action that need to be coordinated to achieve the overall goals of a task. For example, this could require attentional awareness and control in which the subject attends to a primary stimulus channel, but also a secondary channel while ignoring a third class of inputs, i.e. irrelevant distractor stimuli; requiring awareness of the primary stimuli while interleaving attention outside those stimuli to the secondary channel stimuli and not the distractors. For example, in this scenario there would be three different flicker frequencies, for primary task stimuli, secondary task stimuli and distractor stimuli. Subjects can learn to take voluntary control over when to switch attention between primary and secondary stimulus channels and to ignore distractors. The SSVEP/SSAEP measures provide assessment and feedback on attention levels to both primary and secondary tasks and ignoring of distractors.

Training meta-attention is greatly benefited when the stimuli and tasks can be readily related to real-life situations so that the improved attentional awareness and control can be transferred to real world activities more readily. The capability to define which EEG signal corresponds to which stimulus when multiple simultaneous stimuli like these are presented is not possible with other EEG measures (e.g. event related potentials (ERP) or oscillatory signals such as alpha).

Assessment and training can be performed in many different user-defined contexts in their real life. User-defined mental state and external environment can be incorporated into the scoring and computations of attentional control (equations A,B,C and derivatives of these); including comparisons of the magnitudes of attend and ignore ISFs and performance ISFs measured across different time periods (hours, days, weeks etc.). For example, we have shown in the NIH Award study that attend and ignore ISFs increase as a person becomes fatigued at performing a task. Alternatively or in addition, the nature of the external environment can create other forms of distraction that the user can be aware of (quiet office versus noisy bus). Alternatively or in addition, the impact on attention of social factors can be incorporated into assessment and training with this method, including inputs from social media and comparisons with other users or group data.

The within-individual data and across-individual data can be entered into large databases and mined for patterns that inform individual assessment and treatment and for clinical characterization of populations and sub-populations, creation of new clinical types and sub-types and possibly even new clinical classifications; as well as development of new treatments and improvements in personalized treatments.

There are also alternate methods for explicitly and/or implicitly incorporating a target with the attended area, such as superimposing a "target" onto the attended area, by, for example, substantially lengthening/narrowing the duration of the flickering pulse and/or varying the color, shape and/or size of the attended area. It may be useful to also track the error rate by comparing the "correct" responses to targets versus distractors.

Exemplary platforms suitable for implementing embodiments of attention evaluators and/or trainers include desktops, towers, laptops, tablets, smart phones, video gaming systems and training systems such as flight simulators. In addition, suitable visual displays and/or input devices include touchscreens and virtual reality goggles.

For further details of the present invention, please see attached Appendix A.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. In a computerized attention testing system having an EEG sensor and an output device, a method for measuring attention capability comprising:
   providing a first auditory stimulus using an output device to be attended by a user during a time period, the first auditory stimulus pulsating at a first frequency;
   providing a second auditory stimulus using the output device to be ignored by the user during the time period, the second auditory stimulus pulsating at a second frequency;
   measuring an infra-slow fluctuation of SSAEP (Steady State Auditory Evoked Potentials) of the user substantially during the time period using a neural scanner; and
   computing a measure of attention capability of the user by using the infra-slow fluctuation SSAEP of the user.

2. The method of claim 1 wherein the first auditory stimulus includes a first plurality of audible sounds, and wherein the second auditory stimulus includes a second plurality of audible sounds.

3. The method of claim 1 further comprising:
   providing at least one audible target to the user;
   measuring at least one fluctuation of reaction time of the user to the at least one target substantially over the time period; and
   correlating the measured at least one fluctuation of reaction time with the measured SSAEP of the user during the computing of the measure of attention capability of the user.

4. The method of claim 1 wherein the time period is a sustained time period.

5. The method of claim 4 wherein the sustained time period is substantially over ten seconds.

6. The method of claim 1 wherein the SSAEP is measured using an EEG sensor.

7. The method of claim 1 wherein the first frequency is substantially between 3 Hz and 60 kHz.

8. The method of claim 7 wherein the first frequency is substantially between 10 Hz and 20 kHz.

9. The method of claim 1 wherein the second frequency is substantially between 3 Hz and 60 kHz.

10. The method of claim 9 wherein the second frequency is substantially between 10 Hz and 20 kHz.

11. The method of claim 1 wherein a presentation rate of the target is randomized with respect to time.

12. The method of claim 3 further comprising providing at least one audible distractor to be ignored by the user.

* * * * *